United States Patent [19]

Cain, deceased et al.

[11] Patent Number: 4,472,582
[45] Date of Patent: Sep. 18, 1984

[54] 3,5-DISUBSTITUTED-4'-(9-ACRIDINYLAMINO)-METHANE-SULFON-M-ANISIDIDE COMPOUNDS HAVING ANTITUMOR PROPERTIES

[75] Inventors: Bruce F. Cain, deceased, late of Auckland, New Zealand, by Patricia Joyce Cain, executrix; Graham J. Atwell, Auckland, New Zealand; Bruce C. Baguley, Auckland, New Zealand; William A. Denny, Auckland, New Zealand

[73] Assignee: Development Finance Corporation of New Zealand, Wellington, New Zealand

[21] Appl. No.: 386,104

[22] Filed: Jun. 7, 1982

Related U.S. Application Data

[63] Continuation-in-part of Ser. No. 187,517, Sep. 15, 1980, abandoned.

[30] Foreign Application Priority Data

Sep. 14, 1979 [NZ] New Zealand ............. 191577

[51] Int. Cl.³ ............... C07D 219/08; A61K 31/435
[52] U.S. Cl. .................................... 546/106; 424/257
[58] Field of Search ..................... 424/257; 546/106

[56] References Cited

U.S. PATENT DOCUMENTS 4,366,318 12/1982 Cain et al. ............. 546/106

FOREIGN PATENT DOCUMENTS 0025705 3/1981 European Pat. Off. ............. 424/257
0039224 11/1981 European Pat. Off. ............. 424/257

OTHER PUBLICATIONS

Cain et al., J. Med. Chem., vol. 17(9), pp. 922-930, (1974).
Cain et al., J. Med. Chem. vol. 19(12), pp. 1409-1416, (1976).
Cain et al., J. Med. Chem., vol. 20(8), pp. 987-996, (1977).
Ferguson et al., J. Med. Chem., vol. 22(3), pp. 251-255, (3/79).
Denny et al., J. Med. Chem., vol. 22(12), pp. 1453-1460, (12/79).
Ferguson et al., J. Med. Chem., vol. 23(3), pp. 269-274, (3/80).
Baguley et al., J. Med. Chem., vol. 24(5), pp. 520-525, (5/81).

*Primary Examiner*—Donald G. Daus
*Assistant Examiner*—Diana G. Rivers
*Attorney, Agent, or Firm*—Brumbaugh, Graves, Donohue & Raymond

[57] ABSTRACT

3,5-Disubstituted-4'-(9-acridinylamino)-methane-sulfon-m-anisidide compounds represented by the general formula

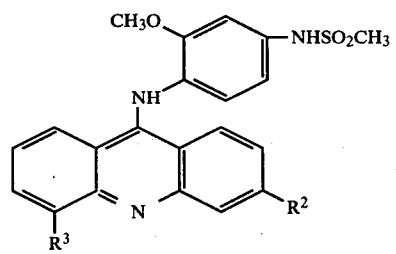

in which $R^2$ and $R^3$ represent, respectively, $-CH_3$ and $-CONHCH_3$, $-CH_3$ and $-CONHCH_2CONH_2$, $-Cl$ and $-CONHCH_2CONH_2$, $-CONHCH_3$ and $-CH_3$; and acid addition salts thereof have unexpectedly high antitumor activity in leukemic animals and low or no direct mutagenicity.

5 Claims, No Drawings

3,5-DISUBSTITUTED-4'-(9-ACRIDINYLAMINO)-METHANE-SULFON-M-ANISIDIDE COMPOUNDS HAVING ANTITUMOR PROPERTIES

This application is a continuation-in-part application of U.S. application Ser. No. 187,517, filed Sept. 15, 1980 (now abandoned).

BACKGROUND OF THE INVENTION

A number of acridinylaminomethanesulfonanilide derivatives have recently been studied for antitumour activity. AMSA or 4'-(9-acridinylamino) methanesulfonanilide was found to show high antitumour activity in L1210 leukemia screening systems (see G. J. Atwell, B. F. Cain and R. N. Seelye, *J. Med. Chem.*, 15, 611–615 (1972)). Of the derivatives of AMSA which have been studied, m-AMSA or 4'-(9-acridinylamino)-methanesulfon-m-anisidide has been shown to be highly effective in treating L1210 leukemia and has shown promise in a number of other experimental tumour systems (see the following articles: B. F. Cain and G. J. Atwell, *Europ. J. Cancer*, 10, 539–549 (1974); B. F. Cain, G. J. Atwell and W. A. Denny, *J. Med. Chem.*, 18, 1110–1117 (1975); B. F. Cain, W. R. Wilson and B. C. Baguley, *Molecular Pharmacology*, 12, 1027–1035 (1976); B. F. Cain, G. J. Atwell and W. A. Denny, *J. Med. Chem.*, 19, 772–777 (1976); B. F. Cain and G. J. Atwell, *J. Med. Chem.*, 19, 1409–1416 (1976); M. J. Waring, *Europ. J. Cancer*, 12, 995–1001 (1976); B. C. Baguley, W. R. Wilson, L. R. Ferguson and B. F. Cain, *Current Chemotherapy*, pp. 1210–1212 (1978); W. A. Denny, G. J. Atwell and B. F. Cain, *J. Med. Chem.*, 21, 5–10 (1978)).

m-AMSA has been selected for clinical trials and has generated clinical interest during Phase I clinical trials (see D. D. Von Hoff and others, *Cancer Treatment Reports*, 62, No. 10, 1421–1426 (1978); S. S. Legha and others, *Cancer Research*, 38, 3712–3716 (1978); and B. F. Cain, U.S. patent application Ser. No. 78,504).

AMSA and m-AMSA have the structural formulae

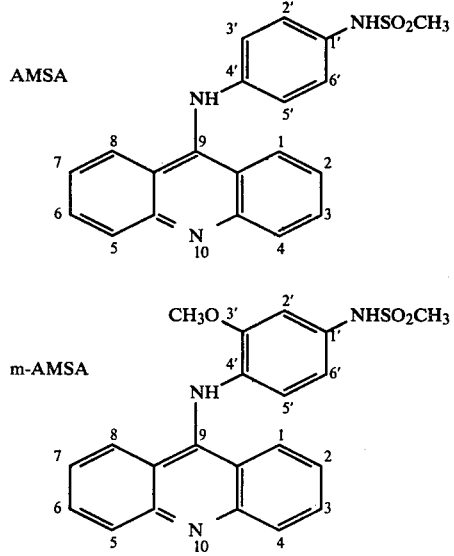

The antitumour activity of a large range of AMSA and m-AMSA analogs containing variously substituted acridine nuclei has now been investigated, (see for example G. J. Atwell, B. F. Cain and R. N. Seelye, *J. Med. Chem.*, 15, 611–615 (1972); B. F. Cain, R. N. Seelye and G. J. Atwell, *J. Med. Chem.*, 17, 922–930 (1974); B. F. Cain, G. J. Atwell and W. A. Denny, *J. Med. Chem.*, 18, 1110–1117 (1975), and *J. Med. Chem.*, 19, 772–777 (1976); B. F. Cain and G. J. Atwell, *J. Med. Chem.*, 19, 1124–1129 and 1409–1416 (1976); G. J. Atwell, B. F. Cain and W. A. Denny, *J. Med. Chem.*, 20, 520–526, 987–996, 1128–1134, and 1242–1246 (1977); W. A. Denny, G. J. Atwell and B. F. Cain, *J. Med. Chem.*, 21, 5–10 (1978); W. A. Denny and B. F. Cain, *J. Med. Chem.*, 21, 430–437 (1978); B. F. Cain, B. C. Baguley and W. A. Denny, *J. Med. Chem.*, 21, 658–668 (1978) and L. R. Ferguson and W. A. Denny, *J. Med. Chem.*, 22, 251–255 (1979)).

As clinical cancer chemotherapy improves, and patients live symptom free for longer intervals, it is obviously important that the agents employed are not carcinogenic and capable of disease re-induction. Employing mutagenicity in the Ames bacterial tester strains (B. N. Ames, J. McCann, and E. Yamasaki, *Mutat. Res*, 31, 347 (1975)) as likely predictors of carcinogenicity, it was apparent that mutagenic activity and antitumour effectiveness did not parallel one another. Such observations suggested that the undesirable side effect of mutagenicity might therefore be eliminated.

SUMMARY OF THE INVENTION

The present invention provides new m-AMSA analogs, namely, for novel 3,5-disubstituted m-AMSA compounds containing a carboxamide substituent in the 3 or 5 positions in the acridine nucleus which have unexpectedly high antitumour activity in leukemic animals and low or no direct mutagenicity.

It is the object of the present invention to provide such compounds, a process for the preparation of these compounds, and the use of the compounds as antitumour agents.

DESCRIPTION OF THE INVENTION

The four novel 3,5-disubstituted m-AMSA compounds of the present invention are represented by the general formula

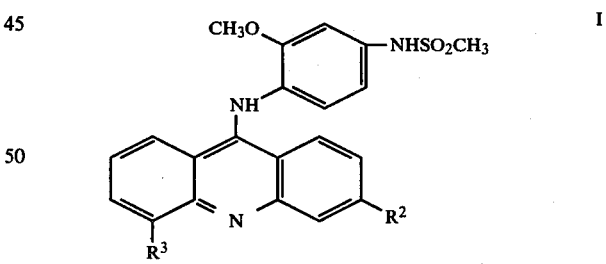

in which $R^2$ and $R^3$ represent, respectively, —CH$_3$ and —CONHCH$_3$, —CH$_3$ and —CONHCH$_2$CONH$_2$, —Cl and —CONHCH$_2$CONH$_2$, —CONHCH$_3$ and —CH$_3$; and acid addition salts thereof.

A preferred group of compounds of formula (I) are those in which $R^2$ represents —CH$_3$ and $R^3$ represents —CONHCH$_3$, or $R^2$ represents —CONHCH$_3$ and $R^3$ represents —CH$_3$, i.e. the isomeric 3-methyl-5-methylcarboxamido and 5-methyl-3-methylcarboxamido compunds. An especially preferred group of compounds of formula (I) are those in which $R^2$ represents —CH$_3$ and $R^3$ represents —CONHCH$_3$, or $R^2$ represents —CH$_3$ and $R^3$ represents —CONHCH$_2$CONH$_2$, because of their unusually high antitumour activity in leukemic animals.

The four compounds of formula (I) form salts with acids. As examples of acid addition salts, there may be mentioned the pharmaceutically acceptable acid addition salts formed with hydrochloric, hydrobromic, lactic, methanesulphonic, D-gluconic, and 2-hydroxyethanesulphonic (i.e. isethionic) acids.

The four compounds of formula (I), and acid addition salts thereof, may be prepared by a process which comprises coupling a 9-chloroacridine of the general formula

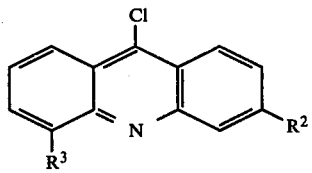

wherein $R^2$ and $R^3$ are as respectively defined above, with p-aminomethanesulfon-m-anisidide having the formula

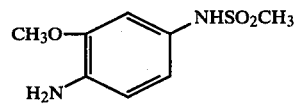

in an acid medium, and, if desired, converting a compound of formula (I) into an acid addition salt thereof.

The coupling of a 9-chloroacridine with the p-aminomethanesulfon-m-anisidide may be performed in aqueous or anhydrous solvents for the reactants and preferably at temperatures between 30° and 100° C. As an example of coupling in an aqueous solvent, a 9-chloroacridine and the p-aminomethanesulfon-m-anisidide in approximately equal molar proportions are dissolved in a minimum volume of boiling EtOH-H$_2$O(2:1 v/v). The components should be completely dissolved before adding the acid catalyst. Concentrated HCl is added to the solution in a quantity sufficient to convert the anisidide to its hydrochloride plus a further 0.1 of this quantity of concentrated HCl. After checking that the reaction mixture has a pH below 6, boiling is continued for 40–45 minutes. In many cases the product crystallises from the reaction mixture, but more commonly EtOH is removed in vacuo and the product salted out with NaCl or NaBr. The crude product, obtained by filtration or by evaporation, is dissolved in EtOH-H$_2$O, filtered from a trace of acridone, and crystallised by addition of a salt of the anion of the desired acid addition salt, and/or by removal of some EtOH.

Coupling in refluxing aqueous ethanol usually provides acceptable yields. In some cases, however, low yields are found to result from competing hydrolysis of the chloroacridine to acridone, and coupling in anhydrous solvents then provides acceptable yields. Essentially the same conditions are used as in the first method except that an anhydrous solvent, for example ethanol, 2-ethoxyethanol or phenol, preferably N-methylpyrrolid-2-one, is used and methanesulphonic acid is used as catalyst. The 9-anilino acridine salts are usually insoluble in the anhydrous media and crystalline during the course of the reaction.

The p-aminomethanesulfon-m-anisidide of formula (III) may be prepared by either of two methods. In the first method 3-methoxy-4-nitroaniline is acylated with methanesulfonyl chloride and the nitro function in the resulting p-nitromethanesulfon-m-anisidide is reduced (Fe/H$^+$). For example, methanesulfonyl chloride may be slowly added to the 3-methoxy-4-nitroaniline in pyridine solution so that the temperature of the solution remains below −5°. The reduction (Fe/H$^+$) of the p-nitromethanesulfon-m-anisidide provides the required p-aminomethanesulfon-m-anisidide.

In the second method 2-methoxy-4-nitroaniline is first converted to 2-methoxy-4-nitroacetanilide, the nitro group is reduced and the amine function so generated acylated with methanesulfonyl chloride. Hydrolytic removal of the protecting acetyl function from the resulting p-acetamidomethanesulfon-m-anisidide then provides the required p-aminomethanesulfon-m-anisidide. The 2-methoxy-4-nitroaniline may be converted to the 2-methoxy-4-nitroacetanilide by literature described methods and then reduced (Fe/H$^+$) to the 4-acetamidoaniline. Further reaction with methanesulfonyl chloride as in the first method produces the p-acetamidomethanesulfon-m-anisidide. The masking acetyl function may be removed by heating under reflux with 2N HCl-EtOH until TLC shows reaction is complete; usually one hour proves sufficient. After removal of solvent and excess HCl in vacuo the free amine product may be precipitated by trituration of the residual hydrochloride with saturated aqueous NaOAc.

The 9-chloroacridines of formula (II) may be prepared by an Ullmann reaction of a substituted 2-halobenzoic acid and a substituted aniline to provide a substituted diphenylaminecarboxylic acid, followed by ring closure and conversion of the substituted 9(10H)-acridone obtained to the substituted 9-chloroacridine. One of the 2-halobenzoic acid and aniline intermediates employed must bear an additional carboxylic acid group for subsequent conversion to the carboxamide substituent in the compound of formula (I). When anthranilic acid is employed as the substituted aniline in the Ullmann reaction, the resulting diphenylaminedicarboxylic acid yields, on acridone ring closure, a mixture of isomers which must be separated. The carboxylic acid group in the 9(10H)-acridone may be converted to a carboxamide group $R^2$ or $R^3$ before coupling the 9-chloroacridine and p-aminomethanesulfon-m-anisidide or it may be protected during the coupling reaction and be subsequently converted to a carboxamide group.

The ring closure of the substituted diphenylaminecarboxylic acid may be effected with POCl$_3$, H$_2$SO$_4$, PPA, or PPE and the substituted 9(10H)-acridone may be converted to the 9-chloroacridine using either POCl$_3$ or SOCl$_2$ containing catalytic quantities of dimethylformamide.

Treatment of the 9(10H)-acridone containing a carboxylic acid group with SOCl$_2$-DMF provides the 9-chloroacridine acid chloride. In anhydrous media at low temperatures ammonia and aliphatic amines react selectively with the acid chloride moiety to provide the 9-chloroacridine carboxamide which may then be coupled with the p-aminomethanesulfon-m-anisidide under mild acid conditions.

Alternatively the 9(10H)-acridone containing a carboxylic acid group may be treated with nitrophenol or tris(4-nitrophenyl) phosphite in pyridine solution to provide the nitrophenyl ester. Treatment of the 9(10H)-acridone nitrophenyl ester with SOCl$_2$-DMF yields the 9-chloroacridine nitrophenyl ester which may be coupled with the p-aminomethanesulfon-m-anisidide in acid media, and then reacted with ammonia or an aliphatic amine to provide the desired carboxamide group containing compound of formula (I).

The following Table I sets out physical data of the four compounds (Compounds Nos. 1-4) within the general formula (I) and preparable by the process of the invention. In Table I the following terms and abbreviations are used:

Anion=the anionic component of the acid addition salt form of the compound of formula (I), which provides adequate solubility for biological screening of the compound.

FB=the free base form of the compound of formula (I)

MW=molecular weight pK=the basic $pK_a$ for the compound as measured spectrophotometrically in 20% aqueous dimethylformamide.

$R_m$=a measure of the compound's lipophilichydrophilic balance from reversed phase chromatography. $R_m$ is linearly related to partition coefficients obtained in the 1-octanol/$H_2O$ system.

then dried. Recrystallisation from dimethylformamide provided pure compound as yellow needles of mp 279°–281° C.

This acridone (20 g) was converted to the corresponding 9-chloro compound by boiling with $SOCl_2$ (60 ml) and dimethylformamide (0.2 ml) for 30 minutes. After removal of $SOCl_2$ in vacuo, the chloro-compound was suspended in cold $CHCl_3$ (250 ml) and a cold (0°–5° C.) solution of 3-methoxy-4-aminomethanesulfonanilide (12.2 g) in N-methylpyrrolid-2-one (100 ml) and 65% aqueous ethanol (30 ml). The mixture was stirred vigorously while warming to the boil and, after addition of 100 ml of 25% aqueous NaCl, $CHCl_3$ removed by distillation at atmospheric pressure. The crystalline ester was collected from the cooled mixture as deep red needles of mp 239°–241° C.

Compound 1 (Table I).

The foregoing nitrophenylester (34 g) was suspended in dimethylformamide (100 ml) and 24% aqueous methylamine (75 ml) stirred in. A homogenous solution rapidly resulted and, after 10 minutes stirring, water (100 ml) was added followed by 10% aqueous $KHCO_3$ (1 liter). The precipitated crystalline base was dissolved

TABLE I

| Compound No. | Substituents in Formula (I) | | Anion | Formula | MP° C. | M.W. | pK | $R_m$ |
|---|---|---|---|---|---|---|---|---|
| | $R^2$ | $R^3$ | | | | | | |
| 1 | $CH_3$ | $CONHCH_3$ | Cl | $C_{24}H_{23}N_4O_4S \cdot HCl$ | 311 (dec) | 500.0 | 6.60 | 0.32 |
| 2 | $CH_3$ | $CONHCH_2CONH_2$ | Cl | $C_{25}H_{25}N_5O_5S \cdot HCl$ | 254–256 | 544.3 | 6.58 | −0.32 |
| 3 | Cl | $CONHCH_2CONH_2$ | Cl | $C_{24}H_{22}ClN_5O_5S \cdot HCl$ | 248–251 (dec) | 563.5 | 5.71 | −0.23 |
| 4 | $CONHCH_3$ | $CH_3$ | Cl | $C_{24}H_{24}N_4O_4S \cdot HCl$ | 312 (dec) | 503 | 6.64 | −0.17 |

The following Examples A and B illustrate the preparation of compounds of the general formula (I).

EXAMPLE A

Production of Compound 1 of Table I 2-((2-Hydroxycarbonyl)anilino)-4-methylbenzoic acid 2-Bromo-4-methylbenzoic acid (43 g) (alternatively 2-chloro-4-methylbenzoic acid), anthranilic acid (30 g), anhydrous $K_2CO_3$ (42 g), catalytic Cu powder (0.05 g) suspended in 2-ethoxyethanol (250 ml) were heated together with stirring under reflux conditions in an oil bath at 160° C. for 1 hour. To the cooled mixture, water (500 ml) was added and stirring continued until all salts had dissolved. The clarified solution was poured into excess 2N HCl and the precipitated crude product collected, well washed with boiling water then dried. Crystallisation from ethyl acetate provided pure product as yellow needles of mp 302°–304° C.

3-Methyl-9(10H)acridone-5-carboxylic acid

The above diacid (50.0 g) was stirred with 98% $H_2SO_4$ (150 ml) while heating in a boiling water bath for 2 hours. The clear solution was carefully poured into water (1.5 liters) and the precipitated acid collected, washed well with water and dried. Repeated crystallisation from ethanol, monitoring by TLC, led to the removal of the unwanted 1-methyl-9(10H)acridone-4-carboxylic acid. The desired product was obtained as yellow needles of mp 337°–338° C. 3-Methyl-5-(4-nitrophenoxycarbonyl)-9(10H)acridone, was prepared by dissolving 3-methyl-9(10H)acridone-5-carboxylic acid (7 g) and 4-nitrophenol (6.35 g) in boiling pyridine (45 ml), cooling to 45° C., adding $PCl_3$ (1.33 ml), then reheating to boiling. During heating the desired nitrophenyl ester crystallised and, after thorough cooling, was collected, washed well with water and methanol, and in boiling 1N acetic acid and NaCl added to the hot solution until the desired hydrochloride salt started to separate. The salt collected from the cooled mixture was purified by solution in hot 0.1N acetic acid, clarification and increase of chloride ion concentration in the hot solution by addition of NaCl until crystallisation initiated. Pure product was obtained as orange needles of mp 311° C.

EXAMPLE B

Production of Compound 4 of Table I 2-(2-Methylanilino)-benzene-1,4-dicarboxylic acid Bromoterephthalic acid (12.2 g), ortho-toluidine (10.7 ml), anhydrous $K_2CO_3$ (13.8 g), catalytic Cu powder (0.2 g) in 2-ethoxy-ethanol (17.5 ml) were stirred together while heating under reflux conditions in an oil bath at 150° C. After 6 hours, water (200 ml) was added and, when all salts had dissolved, the solution was clarified and crude product precipitated by acidification to pH 2. The collected diacid was well washed with boiling water then recrystallised from 50% ethanol, pure product being obtained as yellow needles of mp 318° C. (dec).

4-Methyl-9(10H)acridone-6-carboxylic acid

The above diacid (10 g) was suspended in $POCl_3$, (20 ml) and the mixture boiled under reflux conditions until homogenous, then for ½ hour further. Excess $POCl_3$, was removed in vacuo at 100° C. and to the well cooled syrupy mixture ice-water (80 ml) and acetic acid (20 ml) were added and the mixture heated on a steam bath for 2 hours. Following thorough cooling the acridone-acid was collected, washed well with water, dried, then crystallised from dimethylformamide-water. Pure compound was obtained as yellow needles of mp 241° C. (dec).

Compound 4 (Table I).

4-Methyl-9(10H)acridone-6-carboxylic acid (12.65 g) was suspended in $SOCl_2$ (40 ml) containing dimethylformamide (0.2 ml) and the mixture heated under reflux conditions for 2 hours. Excess $SOCl_2$ was removed in vacuo and the residual chloro-acid chloride dissolved in $CHCl_3$ (40 ml) and this solution added slowly to 24% aqueous methylamine (200 ml) maintaining the temperature of this below 5° C. The precipitated 4-methyl-6-methylcarbamoyl-9-chloroacridine was collected, washed with a little cold $CHCl_3$, then water and dried.

To a solution of the aforementioned compound (14.25 g) in 65% aqueous ethanol (250 ml) was added 3-methoxy-4-aminomethanesulfonanilide (10.8 g) and the mixture stirred till homogenous, acid catalyst (12N HCl; 0.2 ml) added and the solution boiled for 12 minutes, then solvents removed in vacuo. The residual Compound 4 hydrochloride was recrystallised from hot water with the addition of NaCl to depress solubility. Pure compound was obtained as scarlet needles of mp 312° C.

The four compounds represented by the general formula (I) have unexpectedly high antitumour activity in leukemic animals and low or no direct mutagenicity. The compounds are therefore indicated for use as antitumour or anticancer agents and may be formulated in pharmaceutical forms conventional for the administration of such agents to patients.

Accordingly, the present invention also provides pharmaceutical compositions having antitumour activity and comprising at least one compound of the general formula (I), or a pharmaceutically acceptable acid addition salt thereof, and one or more pharmaceutically acceptable carriers or diluents.

In a further aspect, the present invention provides a method for treating tumors and in particular cancers in a patient which comprises administering to the patient a compound of the general formula (I), or a pharmaceutically acceptable acid addition salt thereof.

Possible criteria by which tumor inhibitory analogs of m-AMSA may be judged relative to m-AMSA are:
(1) experimental antitumor effectiveness;
(2) dose potency;
(3) pharmacokinetic properties;
(4) patterns of cross resistance;
(5) tumour spectrum of action;
(6) ease of formulation; and
(7) side effects, including mutagenicity and carcinogenicity.

Data from L1210 leukemia screens has been employed to select active analogs of m-AMSA on the basis of factors (1) to (3), at least in regard to this experimental tumor system. Of available experimental tumors, the L1210 leukemia has the best record for clinical predictability (A. Goldin, A. A. Serpic and N. Mantel, *Cancer Chem. Rep*, 55, 291–298 (1971)) and provides data of recognised value to the American National Cancer Institute. It has also been a primary research aim to develop quantitative molecular structure-biological activity relationships (QSAR) with a view to illuminating fundamental drug properties contributing to biological activity and possibly to aid in prediction of more active drug species. For both sorting purposes and development of QSAR, suitably accurate measures of antileukemic effectiveness are required. An antileukemic screening protocol and following data manipulation method, which avoids common interpretational errors and provides suitably accurate measures of effectiveness is as follows:

In initial screening a standard drug administration schedule has been employed (ip, qd 1–5) and mice ($C_3H/DBA_2$ F1 hybrids) bred in the laboratory, receive a standard tumor inoculum of $10^5$ L1210 cells ip on day 0. After range finding experiments, an LD10 dose has then been derived employing doses separated by 0.05 log.dose units, an acceptable soluble drug formulation (B. F. Cain, R. N. Seelye and G. J. Atwell, *J. Med. Chem.*, 17, 922–930 (1974)) and groups of six tumored mice at each dose level. Deaths occuring before day 8 have been taken as resulting from drug toxicity. From the linear regression relating percent probit-mortality and the logarithms of the corresponding doses, an LD10 value has been derived. Profiles of antileukemic activity have been obtained employing doses separated by 0.09 log.dose intervals. Significant percentage increases in life span of leukemic animals, obtained at and below the LD10 dose, have been linearly correlated with the logarithms of the corresponding doses. The increase in life span (ILS) specified by the life extension-log.dose regression line at the measured LD10 provides a representative measure of antileukemic effectiveness at a standard host load in toxicity (W. A. Denny and B. F. Cain, *J. Med. Chem.*, 21, 430–437 (1978)). For congener selection ILS has been employed as a measure of factor (1) above and LD10 for factor (2). Desirable drug pharmacokinetic properties (factor (3)) have been screened for by employing standard ip drug administration and implanting tumor more remotely; either subcutaneously (sc) or intracerabrally (ic) (B. F. Cain and G. J. Atwell *Europ J. Cancer*, 10, 539 549 (1974), B. F. Cain and G. J. Atwell, *J. Med. Chem.*, 19 1409–1416 (1976)).

Tumor spectrum of action, factor (5), has been examined in a panel of available experimental tumors consisting of L1210 and P388 Leukemias; P815 mastocytoma; B16 melanoma; Lewis lung; transplants of spontaneous mammary tumors arising in C3H mice; drug resistant tumor strains, e.g. L1210/Ara-C; and P388/Adr. Available data show that the L1210 active m-AMSA analogs examined are effective against this total panel, with the exception of the adriamycin resistant P388/Adr. It appears that effectiveness of the individual compounds against these various tumors depends on the site of tumor implantation; mode of drug administration; the pharmacokinetics of the compounds and the intrinsic activity of any drug in the L1210 system.

AMSA does not contain the 3'-methoxyl function of m-AMSA. The 3'-methoxyl function when incorporated into a large range of AMSA analogs containing variously substituted acridine nuclei, has almost invariably provided a valuable increase in dose-potency without loss of antitumor effectiveness.

Multiple regression analysis of accumulated ILS value for totalled agents demonstrates that significant variance is accommodated by regression equations containing:
(a) binomial terms in $R_m$ values;
(b) measures of drug-DNA binding for those agents in which different acridine substituents are employed;
(c) electron density at the 5'-position, as afforded by the summation of Hammett's sigma constants ($\Sigma\delta$) for substituents attached to the 9-anilino ring system.

The DNA employed for measurement of drug-binding is apparently unimportant with these particular congeners; the values measured for different DNAs (CT;AT;GC) are highly covariant. These developed QSAR are important since they strongly suggest that these agents act by intercalating the acridine nucleus into the DNA of the target cancer cell (M. J. Waring *Europ. J. Cancer*, 12, 995–1001 (1976)) and the 9-anilino ring then contacts a further crucial tumor cell component. These analyses clearly demonstrate that most tumor inhibitory and the most dose potent agents result when acridine substituents are employed which augment DNA binding. When multiple acridine substituents are employed, strongest DNA binding has been observed with 3,5-disubstituted variants. In the present invention attention has accordingly been focused on the 3,5-disubstituted m-AMSA analogs.

The quantitative measures of mutagenicity employed in the present studies are those detailed in L. R. Ferguson and W. A. Denny, *J. Med. Chem.*, 22, 251–255 (1979) of early QSAR developed in this area. Further unpublished research has shown that in vitro mutagenicity in the Ames' systems varies according to substitution pattern in an as yet unpredictable fashion. It has been found that, for unknown reasons, an acceptably placed acridine-$CONR^bR^c$ substituent markedly reduces, and in some cases abolishes, mutagenicity but permits full antitumor effectiveness to be retained. Direct mutagenicity in the Ames TA98, TA100, TA1537 assay systems is lower or absent in the 3,5-disubstituted m-AMSA analogs in which one substituent is a —$CONR^bR^c$ group. Available drug examples suggest that —$CONH_2$ variants are considerably less water soluble than the —$CONHR^a$ congeners and the limited —$CONR^bR^c$ examples are markedly less dose potent. In the present invention there has therefore been selected the compounds of the general formula (I) hereinbefore defined which are m-AMSA analogs in which one of the substituents in the 3 and 5 positions is a —$CONHR^a$ group, i.e. a —$CONHCH_3$ group or a —$CONHCH_2CONH_2$ group. Of the acceptable additional substituents which may be employed, and which are represented by $R^2$ or $R^3$ in the general formula (I), a methyl group appears to confer greatest antitumor activity, dose potency and water solubility. For the above reasons, the presently preferred compounds of formula (I) are the two isomeric 3-methyl-5-methylcarboxamido and 5-methyl-3-methylcarboxamido variants. These two preferred compounds are easily formulable, have high experimental antitumor activity, good dose potency, lack significant mutagenic activity in the in vitro Ames systems and inhibit intra-cerebrally implanted L1210 whereas m-AMSA does not. Preliminary data suggests that the 3-methylcarboxamido-5-methyl isomer may have superior antitumor activity. Especially preferred compounds of formula (I) are those in which $R_2$ represents —$CH_3$ and $R^3$ represents —$CONHCH_3$, or $R^2$ represents —$CH_3$ and $R^3$ represents —$CONHCH_2CONH_2$, because of their unusually high antitumour activity in leukemic animals.

The following Table II gives updated biological data of the four compounds (Compounds Nos. 1–4) whose physical data have been given in Table I, and corresponding biological data for m-AMSA for comparison purposes. In Table II the following terms and abbreviations are used:

CT, AT and GC=are relative, inverse measures of compound—DNA binding for calf thymus DNA (CT); poly.dAT (AT) and poly. dGC (GC). (B. C. Baguley and E. M. Falkenhaugh, *Nucleic Acids Res.*, 5, 161–171 (1978), B. F. Cain, B. C. Baguley and W. A. Denny, *J. Med. Chem.*, 21, 658–668 (1978)).

D50 and M50=quantitative measures derived from mutagenicity assays in TA1537 strain of Salmonella typhimurium, defined in L. R. Ferguson and W. A. Denny, *J. Med. Chem.*, 22, 251–255 (1979). (The values of M50 are percentage mutation frequencies at the $D_{50}$ ($\times 10^4$).)

ILS and LD10=as defined above.

D40=the drug dose necessary to provide 40% ILS in standard L1210 assays.

*=available data not as yet allow a firm value to be provided.

TABLE II

| Compound No. | CT | AT | GC | Mutagenicity $D_{50}$ | $M_{50}$ | Tumour L1210-ip Strain F1 Schedule qd 1-5 | | | Tumour L1210-sc Strain F1 Schedule qd 1-5 | | |
|---|---|---|---|---|---|---|---|---|---|---|---|
| | | | | | | LD10 | ILS | D40 | LD10 | ILS | D40 |
| 1 | 5.53 | 4.74 | 2.76 | 15.3 | 1.0 | 12 | 200 | 3 | 10 | 30 | — |
| 2 | 6.53 | 6.53 | 1.84 | 27.6 | 0 | 120 | 200 | 10 | 120 | 50 | 60 |
| 3 | 12e | 13e | 4.91 | 12.4 | 0 | 300 | 120 | 25 | 330 | 65 | 175 |
| 4 | * | 3.2 | * | 43.8 | 0.16 | 20 | 150 | 1 | 25 | 100 | 15 |
| m-AMSA | 10.8 | 10 | 14 | 24.9 | 4 | 9 | 111 | 2.5 | 10 | 45 | 8.0 |

As noted hereinabove, the four 3,5-disubstituted m-AMSA compounds of the invention (Compounds Nos. 1–4) have unexpectedly high antitumour activity in leukemic animals as shown by the observed ILS values given in Table II above (Tumour L1210-i.p., Strain F1, Schedule qd 1-5) and particularly as shown by the difference between the observed ILS values and the predicted ILS values of Compounds Nos. 1–4 set forth in Table III below versus such difference of other comparative disubstituted and trisubstituted m-AMSA compounds (Compounds Nos. C1–C32) set forth in Table IV below. The predicted ILS values in Tables III and IV are obtained by taking the average of the observed ILS values of the corresponding monosubstituted m-AMSA compounds (Compounds Nos. M1–M16) set forth in Table V below.

TABLE III

| Compound No. | 3,5-Disubstituted m-AMSA Substituents | ILS Observed | ILS Predicted | Difference in ILS |
|---|---|---|---|---|
| 1 | 3-$CH_3$,5-$CONHCH_3$ | 200 | 112 | 88 |
| 2 | 3-$CH_3$,5-$CONHCH_2CONH_2$ | 200 | 93 | 107 |
| 3 | 3-Cl,5-$CONHCH_2CONH_2$ | 120 | 85 | 35 |
| 4 | 3-$CONHCH_3$,5-$CH_3$ | 150 | 102 | 48 |

TABLE IV

| Compound No. | Di- and Tri-Substituted m-AMSA Substituents | ILS Observed | ILS Predicted | Difference in ILS |
|---|---|---|---|---|
| C1 | 2-$NH_2$,3-Br | 90 | 113 | −13 |
| C2 | 2-$NH_2$,3-$CF_3$ | 108 | 85 | 23 |
| C3 | 3-$NO_2$,4-$CH_3$ | 54 | 98 | −44 |
| C4 | 3,4-$(CH_3)_2$ | 79 | 100 | −21 |

TABLE IV-continued

| Compound No. | Di- and Tri-Substituted m-AMSA Substituents | ILS Observed | ILS Predicted | Difference in ILS |
|---|---|---|---|---|
| C5 | 3-$NO_2$,5-$CH_3$ | 107 | 98 | 9 |
| C6 | 3-$NO_2$,5-$OCH_3$ | 66 | 97 | −31 |
| C7 | 3-$NH_2$,5-$CH_3$ | 125 | 97 | 28 |
| C8 | 3-I,5-$CH_3$ | 86 | 105 | −19 |
| C9 | 3-I,5-$OCH_3$ | 63 | 104 | −41 |
| C10 | 3-$NHCH_3$,5-$CH_3$ | 68 | 103 | −35 |
| C11 | 3-Cl,5-$CH_3$ | 57 | 92 | −35 |
| C12 | 3-Cl,5-$OCH_3$ | 82 | 91 | −9 |
| C13 | 3,5-$(CH_3)_2$ | 97 | 100 | −3 |
| C14 | 3-$CH_3$,5-$CONH_2$ | 100 | 100 | 0 |
| C15 | 3-Cl,5-$CONH_2$ | 90 | 92 | −2 |
| C16 | 3-$NO_2$,5-$CONH_2$ | 100 | 98 | 2 |
| C17 | 3-$CONH_2$,5-$CH_3$ | 150 | 131 | 19 |
| C18 | 3-$CONH_2$,5-$OCH_3$ | 70 | 130 | −60 |
| C19 | 3,6-$(Cl)_2$ | 52 | 72 | −20 |
| C20 | 3-Cl,6-$CF_3$ | 5 | 68 | −63 |
| C21 | 3,6-$(Br)_2$ | 82 | 119 | −37 |
| C22 | 3-$NO_2$,6-$CH_3$ | 91 | 86 | 5 |
| C23 | 3,6-$(NO_2)_2$ | 58 | 84 | −26 |
| C24 | 4,5-$(CH_3)_2$ | 87 | 111 | −24 |
| C25 | 2-$NH_2$,3,4-$(CH_3)_2$ | 61 | 102 | −41 |
| C26 | 2-$NH_2$,3-Br,5-$CH_3$ | 83 | 112 | −29 |
| C27 | 3-$NO_2$,4,5-$(CH_3)_2$ | 28 | 102 | −74 |
| C28 | 3,4,5-$(CH_3)_3$ | 76 | 103 | −27 |
| C29 | 3,4,6-$(CH_3)_3$ | 58 | 96 | −38 |
| C30 | 3-$NO_2$,5,6-$(CH_3)_2$ | 92 | 94 | −2 |
| C31 | 3-$NH_2$,5,6-$(CH_3)_2$ | 79 | 94 | −15 |
| C32 | 3-$NHCH_3$,5,6-$(CH_3)_2$ | 64 | 98 | −34 |

TABLE V

| Compound No. | Monosubstituted m-AMSA Substituent | ILS Observed |
|---|---|---|
| M1 | 2-$NH_2$ | 106 |
| M2 | 3-$CH_3$ (or 6-$CH_3$) | 88 |
| M3 | 3-$CONH_2$ | 150 |
| M4 | 3-$CONHCH_3$ | 92 |
| M5 | 3-Cl (or 6-Cl) | 72 |
| M6 | 3-Br (or 6-Br) | 119 |
| M7 | 3-I | 98 |
| M8 | 3-$CF_3$ (or 6-$CF_3$) | 63 |
| M9 | 3-$NH_2$ | 82 |
| M10 | 3-$NHCH_3$ | 94 |
| M11 | 3-$NO_2$ (or 6-$NO_2$) | 84 |
| M12 | 4-$CH_3$ (or 5-$CH_3$) | 111 |
| M13 | 4-$CONH_2$ (or 5-$CONH_2$) | 112 |
| M14 | 4-$CONHCH_3$ (or 5-$CONHCH_3$) | 135 |
| M15 | 4-$CONHCH_2CONH_2$ (or 5-$CONHCH_2CONH_2$) | 98 |
| M16 | 4-$OCH_3$ (or 5-$OCH_3$) | 110 |

As shown in Table III above, Compounds Nos. 1 and 2 of the invention, i.e., 3-$CH_3$, 5-$CONHCH_3$-m-AMSA and 3-$CH_3$, 5$CONHCH_2CONH_2$-m-AMSA, have unusually high antitumour activity in leukemic animals, namely, observed ILS values of 200, in comparison with the comparative di- and tri-substituted m-AMSA Compounds Nos. C1–C32 in Table IV which have observed ILS values ranging from only 5 to 150. Moreover, the four Compounds Nos. 1–4 of the invention have unexpectedly high antitumour activity in leukemic animals, namely, a difference between the observed ILS values and the predicted ILS values ranging from 35 for Compound 3 to 107 for Compound 2 (See Table III), in comparison with the comparative di- and tri-substituted m-AMSA Compounds Nos. C1–C32 where the difference between the observed ILS values and the predicted ILS values ranges from −74 to 28 (See Table IV). Table IV also shows that only six of the thirty-two comparative di- and tri-substituted m-AMSA compounds have observed ILS values greater than their predicted ILS values, namely, Compounds Nos. C2, C5, C7, C16, C17 and C22. It should also be noted that the comparative di-substituted m-AMSA Compounds Nos. C14–C18 (Table IV) are 3,5-disubstituted m-AMSA compounds containing a carboxamide substituent in the 3 or 5 positions in the acridine nucleus, as is true of Compounds Nos. 1–4 of the invention (Table III); however, quite unexpectedly the Compounds Nos. 1–4 of the invention have a difference between the observed ILS values and the predicted ILS values ranging from 35 to 107 (Table III), whereas said comparative Compounds Nos. C14–C18 have a difference between the observed ILS values and the predicted ILS values ranging from −60 to 19 (Table IV).

The Compounds Nos. 1–4 of the invention also have observed ILS values greater than that of m-AMSA, namely, 120 to 200 versus 111, and lower $M_{50}$ mutagenicity values, namely, 0 to 1.0 versus 4 (Table II).

What is claimed is:

1. 3,5-disubstituted 4'-(9-acridinylamino)-methanesulfon-m-anisidide compounds represented by the general formula

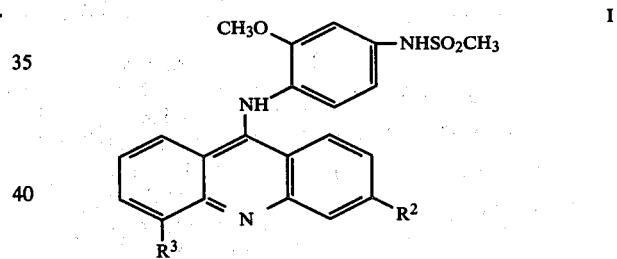

in which $R_2$ and $R_3$ represent, respectively, —$CH_3$ and —$CONHCH_3$, —$CH_3$ and —$CONHCH_2CONH_2$, —Cl and —$CONHCH_2CONH_2$, —$CONHCH_3$ and —$CH_3$; and acid addition salts thereof.

2. A compound according to claim 1 in which $R^2$ and $R^3$ represent, respectively, —$CH_3$ and —$CONHCH_3$.

3. A compound according to claim 1 in which $R^2$ and $R^3$ represent, respectively, —$CH_3$ and —$CONHCH_2CONH_2$.

4. A compound according to claim 1 in which $R^2$ and $R^3$ represent, respectively, —Cl and —$CONHCH_2CONH_2$.

5. A compound according to claim 1 in which $R^2$ and $R^3$ represent, respectively, —$CONHCH_3$ and —$CH_3$.

* * * * *